United States Patent [19]
Rousseau et al.

[11] Patent Number: 5,869,604
[45] Date of Patent: Feb. 9, 1999

[54] CRYSTALLIZATION AND PURIFICATION OF POLYPEPTIDES

[75] Inventors: Ronald W. Rousseau; Athanassios Sambanis; Walter L. Kimble, all of Atlanta, Ga.

[73] Assignee: Georgia Institute of Technology, Atlanta, Ga.

[21] Appl. No.: 555,826

[22] Filed: Nov. 9, 1995

[51] Int. Cl.$^6$ ..................................................... C07K 1/36
[52] U.S. Cl. ........................ 530/344; 530/412; 530/418; 514/2
[58] Field of Search ................... 514/2; 530/344, 530/412, 418

[56] References Cited

U.S. PATENT DOCUMENTS

| | | | |
|---|---|---|---|
| 4,188,318 | 2/1980 | Shanbrom | 260/112 B |
| 4,334,024 | 6/1982 | Johal | 435/232 |
| 4,436,658 | 3/1984 | Peyrouset et al. | 260/122 |
| 4,668,584 | 5/1987 | Uzgiris et al. | 428/408 |
| 4,761,482 | 8/1988 | Schultze | 540/145 |
| 4,857,317 | 8/1989 | Wijnendaele et al. | 424/89 |
| 4,981,952 | 1/1991 | Yan | 530/384 |
| 5,101,018 | 3/1992 | Mehrotra et al. | 530/399 |
| 5,278,284 | 1/1994 | Lusk et al. | 530/305 |
| 5,441,644 | 8/1995 | Kinouchi | 210/651 |
| 5,504,188 | 4/1996 | Baker et al. | 530/304 |
| 5,597,900 | 1/1997 | Hammond et al. | 530/351 |

OTHER PUBLICATIONS

Kimble et al. "Lysozyme crystallization by vapor diffusion: characterization and modeling in the absence and presence of exogenous minerals" *J Crystal Growth* 147:165–171, Jan. 1995.

Givargizov et al. "Artificial epitaxy (graphoepitaxy) of proteins" *J. Crystal Growth* 112:758–772, 1991.

McPherson, Alexander "Macromolecular Crystals" *Scientific American,* pp. 62–69, Mar. 1989.

McPherson et al. "The Use of Heterogeneous and Epitaxial Nucleants to Promote the Growth of Protein Crystals" *J. Crystal Growth* 90:47–50, 1988.

McPherson et al. "Heterogenous and Epitaxial Nucleation of Protein Crystal on Mineral Surfaces" *Science* 239:385–387, Jan. 1988.

McPherson et al. "Facilitation of the Growth of Proteins Crystals by Heterogeneous/Epitaxial Nucleation" *J. Crystal Growth* 85:206–214, 1987.

*Primary Examiner*—Cecilia J. Tsang
*Assistant Examiner*—Patrick R. Delaney
*Attorney, Agent, or Firm*—Needle & Rosenberg, P.C.

[57] ABSTRACT

The invention is directed to a method of highly purifying a polypeptide or other biological compounds from a contaminant by crystallization comprising contacting a mixture containing uncrystallized polypeptides and a contaminant with an exogenous nucleating agent, crystallizing the polypeptides, thereby forming at least one crystal of the polypeptide attached to the nucleating agent, the attached crystal being of a high purity, and at least one polypeptide crystal unattached to the nucleating agent, the unattached crystal being of a lower purity than the attached crystal, and separating the crystal attached to the nucleating agent from the crystal unattached to the nucleating agent. Also, the invention is directed to a method of purifying a polypeptide in a high purity and in a high yield from a contaminant by crystallization comprising contacting a mixture containing uncrystallized polypeptides and a contaminant with an exogenous nucleating agent that has a close lattice match to the polypeptide, crystallizing the polypeptides, thereby forming at least one crystal of the polypeptide attached to the nucleating agent, the attached crystal being of a high purity and produced in a high yield, and at least one crystal unattached to the nucleating agent, the unattached crystal being of a lower purity than the attached crystal, and separating the crystal attached to the nucleating agent from the crystal unattached to the nucleating agent. The invention is also directed to compositions comprising highly purified polypeptide or biological compound crystals and compositions of highly purified polypeptides or biological compounds.

44 Claims, 3 Drawing Sheets

CRYSTALLIZATION AND PURIFICATION OF POLYPEPTIDES

BACKGROUND OF THE INVENTION

1. Field of the Invention

This invention relates generally to a method of purifying biological compounds or molecules, such as polypeptides, by crystallization. More particularly, the compounds can be purified to a significantly higher degree of purity than previously available techniques. In another embodiment, the present invention relates to crystallizing biological compounds on nucleating agents with a close lattice match to the crystalline lattice of the biological compound to selectively obtain biological compound crystals of high purity in a high yield.

2. Background Art

Crystallization of biological compounds, such as polypeptides, is important, both as one of the final separation or purification steps in bioprocessing and for growing crystals for basic scientific studies, such as structural analysis by X-ray diffraction. For example, improvements in protein purity are important to achieve more therapeutically acceptable proteins for drug use and for facilitating or even permitting the study of proteins by, for example, X-ray diffraction for rational drug design. Traditional methods for crystallizing proteins (herein after referred to as polypeptides), such as by spontaneous crystallization wherein no nucleation agent is used, have resulted in high failure rates and high heterogeneity of any resulting crystals. The present invention provides techniques for obtaining biological compound crystals in higher purity than previously attained, or in a combination of a high purity in a high yield never before attainable, based on their attachment to an exogenous nucleating agent.

This invention, therefore, represents a new method of growing biological compound crystals, such as polypeptide crystals, of high purity, and solves a need in the art for producing crystals of high purity, and in one embodiment, in a high purity and in a high yield.

SUMMARY OF THE INVENTION

In accordance with the purpose(s) of this invention, as embodied and broadly described herein, this invention, in one aspect, relates to a method of highly purifying a polypeptide from a contaminant by crystallization comprising contacting a mixture containing uncrystallized polypeptides and a contaminant with an exogenous nucleating agent, crystallizing the polypeptides, thereby forming at least one crystal of the polypeptide attached to the nucleating agent, the attached crystal being of a high purity, and at least one polypeptide crystal unattached to the nucleating agent, the unattached crystal being of a lower purity than the attached crystal, and separating the crystal attached to the nucleating agent from the crystal unattached to the nucleating agent.

The invention further provides a method of purifying a polypeptide in a high purity and in a high yield from a contaminant by crystallization comprising contacting a mixture containing uncrystallized polypeptides and a contaminant with an exogenous nucleating agent that has a close lattice match to the polypeptide, crystallizing the polypeptides, thereby forming at least one crystal of the polypeptide attached to the nucleating agent, the attached crystal being of a high purity and produced in a high yield, and at least one crystal unattached to the nucleating agent, the unattached crystal being of a lower purity than the attached crystal, and separating the crystal attached to the nucleating agent from the crystal unattached to the nucleating agent.

In another aspect, the invention provides for the product made by the methods of the invention.

In another aspect, the invention provides a composition consisting of at least one highly purified polypeptide crystal attached to an exogenous nucleating agent, wherein the polypeptide is not lysozyme, canavalin, concanavalin B, or beef liver catalase.

In another aspect, the invention provides a composition consisting essentially of at least one highly purified polypeptide crystal attached to an exogenous nucleating agent, wherein the polypeptide is not lysozyme, canavalin, concanavalin B, or beef liver catalase.

In another aspect, the invention provides a composition comprising at least one highly purified polypeptide crystal attached to an exogenous nucleating agent, wherein the polypeptide is not lysozyme, canavalin, concanavalin B, or beef liver catalase.

In another aspect, the invention provides a composition consisting of a highly purified polypeptide crystal that has been separated from a nucleating agent, wherein the purity of the crystal is at least 99.85%.

In another aspect, the invention provides a composition consisting essentially of a highly purified polypeptide crystal that has been separated from a nucleating agent, wherein the purity of the crystal is at least 99.85%.

In another aspect, the invention provides a composition comprising a highly purified polypeptide crystal that has been separated from a nucleating agent, wherein the purity of the crystal is at least 99.85%.

In another aspect, the invention provides a composition consisting of a highly purified polypeptide that has been separated from a nucleating agent, wherein the purity of the polypeptide is at least 99.85%.

In another aspect, the invention provides a composition consisting essentially of a highly purified polypeptide that has been separated from a nucleating agent, wherein the purity of the polypeptide is at least 99.85%.

In another aspect, the invention provides a composition comprising a highly purified polypeptide that has been separated from a nucleating agent, wherein the purity of the polypeptide is at least 99.85%.

In another aspect, the invention provides a method of highly purifying a biological compound from a contaminant by crystallization comprising contacting a mixture containing uncrystallized biological compounds and a contaminant with an exogenous nucleating agent, crystallizing the biological compounds, thereby forming at least one crystal of the biological compound attached to the nucleating agent, the attached crystal being of a high purity, and at least one biological compound crystal unattached to the nucleating agent, the unattached crystal being of a lower purity than the attached crystal, and separating the crystal attached to the nucleating agent from the crystal unattached to the nucleating agent.

In another aspect, the invention provides a method of purifying a biological compound in a high purity and in a high yield from a contaminant by crystallization comprising contacting a mixture containing uncrystallized biological compounds and a contaminant with an exogenous nucleating agent that has a close lattice match to the biological compound, crystallizing the biological compounds, thereby forming at least one crystal of the biological compound attached to the nucleating agent, the attached crystal being of a high purity and produced in a high yield, and at least one crystal unattached to the nucleating agent, the unattached crystal being of a lower purity than the attached crystal, and separating the crystal attached to the nucleating agent from the crystal unattached to the nucleating agent.

In another aspect, the invention provides a composition comprising at least one highly purified biological compound crystal attached to an exogenous nucleating agent, wherein the biological compound is not lysozyme, canavalin, concanavalin B, or beef liver catalase.

In another aspect, the invention provides a composition comprising a highly purified biological compound crystal that has been separated from a nucleating agent, wherein the purity of the crystal is at least 99.85%.

In yet another aspect, the invention provides a composition comprising a highly purified biological compound that has been separated from a nucleating agent, wherein the purity of the biological compound is at least 99.85%.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

The accompanying figures, which are incorporated in and constitute a part of this specification, illustrate several embodiments of the invention and together with the description, serve to explain the principles of the invention.

DESCRIPTION OF THE PREFERRED EMBODIMENTS

The present invention may be understood more readily by reference to the following detailed description of preferred embodiments of the invention and the Example included therein and to the Figures and their previous and following description.

Before the present compounds, compositions and methods are disclosed and described, it is to be understood that this invention is not limited to specific methods, specific exogenous nucleating agents, or specific polypeptides, or other specific crystallizable compounds, as such may, of course, vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "a highly purified crystal of the polypeptide" includes multiple highly purified crystals of the polypeptide.

In one aspect, the invention relates to a method of highly purifying a polypeptide from a contaminant by crystallization comprising contacting a mixture containing uncrystallized polypeptides and a contaminant with an exogenous nucleating agent, crystallizing the polypeptides, thereby forming at least one crystal of the polypeptide attached to the nucleating agent, the attached crystal being of a high purity, and at least one polypeptide crystal unattached to the nucleating agent, the unattached crystal being of a lower purity than the attached crystal, and separating the crystal attached to the nucleating agent from the crystal unattached to the nucleating agent.

The invention further provides a method of purifying a polypeptide in a high purity and in a high yield from a contaminant by crystallization comprising contacting a mixture containing uncrystallized polypeptides and a contaminant with an exogenous nucleating agent that has a close lattice match to the polypeptide, crystallizing the polypeptides, thereby forming at least one crystal of the polypeptide attached to the nucleating agent, the attached crystal being of a high purity and produced in a high yield, and at least one crystal unattached to the nucleating agent, the unattached crystal being of a lower purity than the attached crystal, and separating the crystal attached to the nucleating agent from the crystal unattached to the nucleating agent.

In another aspect, the invention provides for the product made by the methods of the invention.

In another aspect, the invention provides a composition consisting of at least one highly purified polypeptide crystal attached to an exogenous nucleating agent, wherein the polypeptide is not lysozyme, canavalin, concanavalin B, or beef liver catalase.

In another aspect, the invention provides a composition consisting essentially of at least one highly purified polypeptide crystal attached to an exogenous nucleating agent, wherein the polypeptide is not lysozyme, canavalin, concanavalin B, or beef liver catalase.

In another aspect, the invention provides a composition comprising at least one highly purified polypeptide crystal attached to an exogenous nucleating agent, wherein the polypeptide is not lysozyme, canavalin, concanavalin B, or beef liver catalase.

In another aspect, the invention provides a composition consisting of a highly purified polypeptide crystal that has been separated from a nucleating agent, wherein the purity of the crystal is at least 99.85%.

In another aspect, the invention provides a composition consisting essentially of a highly purified polypeptide crystal that has been separated from a nucleating agent, wherein the purity of the crystal is at least 99.85%.

In another aspect, the invention provides a composition comprising a highly purified polypeptide crystal that has been separated from a nucleating agent, wherein the purity of the crystal is at least 99.85%.

In another aspect, the invention provides a composition consisting of a highly purified polypeptide that has been separated from a nucleating agent, wherein the purity of the polypeptide is at least 99.85%.

In another aspect, the invention provides a composition consisting essentially of a highly purified polypeptide that has been separated from a nucleating agent, wherein the purity of the polypeptide is at least 99.85%.

In another aspect, the invention provides a composition comprising a highly purified polypeptide that has been separated from a nucleating agent, wherein the purity of the polypeptide is at least 99.85%.

Highly purified polypeptide crystals can be obtained by any of the methods of the invention.

In another aspect, the invention provides a method of highly purifying a biological compound from a contaminant by crystallization comprising contacting a mixture containing uncrystallized biological compounds and a contaminant with an exogenous nucleating agent, crystallizing the biological compounds, thereby forming at least one crystal of the biological compound attached to the nucleating agent, the attached crystal being of a high purity, and at least one biological compound crystal unattached to the nucleating agent, the unattached crystal being of a lower purity than the attached crystal, and separating the crystal attached to the nucleating agent from the crystal unattached to the nucleating agent.

In another aspect, the invention provides a method of purifying a biological compound in a high purity and in a high yield from a contaminant by crystallization comprising contacting a mixture containing uncrystallized biological compounds and a contaminant with an exogenous nucleating agent that has a close lattice match to the biological compound, crystallizing the biological compounds, thereby forming at least one crystal of the biological compound attached to the nucleating agent, the attached crystal being of a high purity and produced in a high yield, and at least one crystal unattached to the nucleating agent, the unattached crystal being of a lower purity than the attached crystal, and separating the crystal attached to the nucleating agent from the crystal unattached to the nucleating agent.

In another aspect, the invention provides a composition comprising at least one highly purified biological compound crystal attached to an exogenous nucleating agent, wherein the biological compound is not lysozyme, canavalin, concanavalin B, or beef liver catalase.

In another aspect, the invention provides a composition comprising a highly purified biological compound crystal that has been separated from a nucleating agent, wherein the purity of the crystal is at least 99.85%.

In yet another aspect, the invention provides a composition comprising a highly purified biological compound that has been separated from a nucleating agent, wherein the purity of the biological compound is at least 99.85%.

In this specification and in the claims which follow, reference will be made to a number of terms which shall be defined to have the following meanings:

It is to be understood that reference to polypeptide crystallization in this invention applies equally as well to other biological molecules or compounds and recitation herein of the more specific "polypeptide" is not intended to be limiting as it also includes the broader category of biological compounds for all aspects of this invention.

The term "mixture" is a term familiar to one of ordinary skill in the art and is used herein to describe, for example, non-solutions, solutions, emulsions, suspensions, concentrates, slurries, and the like.

The term "nucleating agent" is a term familiar to one of ordinary skill in the art and is used herein to describe any material where a solid interface causes a reduction in the critical supersaturation required for crystallization as opposed to spontaneous nucleation of a polypeptide or any other compound that is being crystallized.

The term "exogenous" nucleating agent is used herein to describe any foreign material, or a material of a different type, added to the crystallization mixture to induce crystallization of a polypeptide, but which does not include a crystalline seed of the polypeptide itself.

The term "heterogeneous nucleation" is a term familiar to one of ordinary skill in the art and is used herein to describe nucleation of a polypeptide or other compound being crystallized by initiating crystallization on a solid interface in the crystallization mixture.

The term "epitaxial substrate" is a term familiar to one of ordinary skill in the art and is used herein to describe a type of heterogeneous nucleation where the crystallographic orientation of the polypeptide or other compound being crystallized is restricted to one or few possibilities by the crystallographic orientation of the substrate surface.

The term "crystalline lattice" is a term familiar to one of ordinary skill in the art and is used herein to describe a regularly spaced array of points that represents the structure of the crystal. Crystals are composed of groups of atoms repeated at regular intervals in three dimensions with the same orientation. Each such group of atoms is replaced by a representative point; the collection of points so formed is the lattice of the crystal.

The term "lattice match" is used herein to describe an areal lattice match between the area of the crystalline lattice of the exogenous nucleating agent and the area of the crystalline lattice of the polypeptide or other compound being crystallized. The two interacting lattices do not have to be exact fits to be a "close" lattice match as defined herein. The linear lattice dimension of one crystal face of the unit cell may be integral multiples of the dimensions on the other when calculating the areal lattice match.

The term "unit cell" is a term familiar to one of ordinary skill in the art and is used herein to describe the smallest unit of the lattice that displays the symmetry of the crystalline lattice.

The term "crystal" as used herein is defined to mean one or more single crystals. For example, a single nucleating agent may have one or several attached polypeptide crystals.

The term "majority" as used herein is defined as greater than 50% of the crystals.

As used herein, the term "polypeptide" is intended to include any peptides, oligopeptides, polypeptides, proteins, protein segments, protein domains, enzymes, enzyme segments, enzyme domains, and the like, that are crystallizable. This term is intended to include polypeptide compounds of the same species, or polypeptide compounds of more than one species. Some examples of polypeptides that can be used in this invention include, but are not limited to, chicken egg white lysozyme, albumin, catalase, canavalin, concanavalin B, vicillin, insulin, pepsin, pyruvate kinase, creatine kinase, lactate dehydrogenase, and selenomethionine. The polypeptide is not restricted to a particular size. The polypeptide may be of about 2 amino acids or more, as long as it is crystallizable. Additionally, the polypeptide may be modified. Examples of such modifications include, but are not limited to, post-translational methylation, acetylation, phosphorylation, and glycosylation. Chemical derivatives of polypeptides can also be used in this invention. Such chemical derivatives may include polypeptides attached to other compounds through glutaraldehyde or carbodiimide cross-linking, polypeptides conjugated to a fluorochrome or other moieties, or polypeptides containing modified amino acid residues. Additionally the polypeptides may include those polypeptides together with a ligand or cofactor. Specific examples of this include, but are not limited to, myoglobin together with its associated iron atom, and coenzyme B12 with its associated cobalt atom.

Additionally, other molecules or compounds may be used in this invention as well as polypeptides. A skilled practitioner in the art will readily appreciate that other compounds may be crystallized and purified using the disclosed methods. For example, these other compounds may include, but are not limited to, amino acids, nucleic acid molecules such as tRNA and hybrids between different types of nucleic acids, mono- and polyclonal antibodies, hormones, nucleotides, nucleosides, and toxins, nucleic acid/drug complexes, nucleic acid/polypeptide complexes, histones, ribosomes, and viruses. Specific examples include, but are not limited to, tobacco mosaic virus, poliovirus, and cytomegalovirus.

The present invention provides for crystallizing polypeptides or other biological compounds on an exogenous nucleating agent. Crystallization initiates with a nucleation phase, i.e. the formation of the first ordered aggregates. This formation of the first ordered aggregates, in nucleations other than spontaneous nucleation, is achieved by the presence of a solid interface in the crystalline mixture, which is referred to herein as the exogenous nucleating agent. This surface causes a reduction in the critical supersaturation (or supercooling) required for crystal nucleation. Any such agent that achieves the aforementioned reduction in the critical supersaturation (or supercooling) can be used in the present invention. Such exogenous nucleating agents include, but are not limited to, minerals, transition metal ions such as copper and lead, highly absorbent structures such as zeolites, preformed crystal seeds of amino acids, and preformed crystal seeds of polypeptides other than the polypeptide being crystallized.

More than a single exogenous nucleating agent can be present in a single crystallization mixture. For example, a single crystallization mixture can contain many exogenous nucleating agents of the same type, or even of different types. Each exogenous nucleating agent present in a crystallization mixture can have a single polypeptide crystal attached to it, or have multiple crystals attached to it.

Once mixed with the exogenous nucleating agent, the crystallization of the polypeptide or other compound can be through any number of crystallization procedures that are well known in the art. For example, detailed laboratory procedures are published which present actual methods for crystallizing biological compounds. Typically, crystallization involves lowering the temperature of the mixture containing the polypeptide or increasing the concentration of the polypeptide in the mixture by, for example, removing solvent from the mixture containing the polypeptide through vapor diffusion. Other crystallization techniques include, but are not limited to, batch crystallization, dialysis, gel crystallization, and liquid bridge crystallization. General crystallization conditions are set forth, for example, in *Crystallization of Nucleic Acids and Proteins: A Practical Approach*, ed. A. Ducruix and R. Giegé, Oxford University Press, New York, 1992.

Epitaxial nucleation is a type of nucleation wherein the crystallographic orientation of the crystallizing material is restricted to one or few possibilities by the crystallographic structure of the nucleating substrate surface. This restricted growth orientation of the polypeptide on the nucleating surface is presumably a consequence of the ability of the periodic array of chemical groups exposed on the surface of the nucleating agent to effectively concentrate and organize the crystallizing compounds into an ordered and periodic layer. This initial restricted and organized order then is propagated in the third dimension as more and more crystallizing compounds are added by normal crystal growth mechanisms. Not wishing to be bound by theory, it is believed that nucleation of a polypeptide having a close lattice match to the nucleating agent relates to epitaxial nucleation. These terms, however, are not equivalent. Also not wishing to be bound by theory, it is also believed that a close lattice match may be a prerequisite for epitaxial crystal growth, but crystals can exhibit epitaxial growth on exogenous nucleating agents that do not have a close lattice match to the polypeptide.

The present invention discloses a method of obtaining polypeptide crystals of high purity by using an exogenous nucleating agent that may optionally have a close lattice match, or obtaining polypeptide crystals of high purity and high yield by using an exogenous nucleating agent that has a close lattice match to the polypeptide. The lattice match is determined by the areal dimensions of the two crystals. This areal lattice match calculation is well known to one of skill in the art. See, e.g., McPherson, A. and Shlichta, P. J. Facilitation of the growth of protein crystals by heterogeneous/epitaxial nucleation. J. Crystal Growth 85:206–214 (1987). To calculate the areal lattice match between two crystalline surfaces, the X and Y linear dimensions of a lattice surface of a polypeptide or other biological compound are compared on an area basis to the corresponding X' and Y' linear dimensions of the exogenous nucleating agent. Specifically, the percent mismatch is calculated as follows:

((the lattice area of the exogenous nucleating agent minus the lattice area of the polypeptide or other biological compound), divided by the lattice area of the polypeptide or other biological compound), multiplied by 100, yields a figure. The absolute value of that figure is the percent areal lattice mismatch between the two lattice surfaces. One hundred minus this mismatch figure, therefore, is the percent areal lattice match between the two lattice surfaces.

The lattice dimensions of the crystal face on the nucleating agent and on the biological compound can be integral multiples of one another. This is taken into account in the lattice match calculation. This calculation is not applicable to those exogenous nucleating agents that do not have a definable unit cell; therefore, they do not have a lattice match to the biological compound crystal.

In one embodiment, the present invention provides for purification of polypeptides by crystallization of a polypeptide using a nucleating agent with a close lattice match to the lattice of the polypeptide. The lattice match does not have to be an exact fit to be within the scope of this invention. In particular, the areal lattice match between the respective X and Y coordinates of the nucleating agent and the polypeptide is preferably at least 80% of each other, more preferably within at least 85% of each other, even more preferably within at least 90% of each other, even more preferably within at least 95% of each other, and even more preferably within at least 98% of each other. The lattice dimensions for calculating the lattice area for a number of substrates, including mineral substrates, is readily obtainable to one skilled in the art.

The exogenous nucleating agent with a close lattice match can be any crystalline material that may serve as a nucleating agent and which has a close lattice match to the lattice of a polypeptide. These include, but are not limited to, crystalline forms of minerals, transition metal ions such as copper and lead, highly absorbent structures such as zeolites, preformed crystal seeds of amino acids, preformed crystal seeds of polypeptides other than the polypeptide being crystallized, other biological compounds, and other like crystals.

Typical minerals that can be used include, but are not limited to, apophyllite, lepidolite, topaz, galena, quartz, and microcline, which can be found, for example, in *Lattice Structure of Minerals*, L. G. Berry, et al., in *Mineralogy*, 2nd Ed., W. H. Freeman and Co., San Francisco, Calif. (1983), which is herein incorporated by reference, for all its teachings and for all the specific teachings of typical minerals. Alternatively, mineral surfaces can be artificially synthesized which have a pre-designed lattice structure. These artificial mineral substrates can be created to fulfill a general purpose, or alternatively, to match with a specific protein lattice.

An example of a non-mineral nucleating agent exhibiting close lattice match characteristics to a material being crystallized is a nucleic acid sequence complementary to the nucleic acid being crystallized. This intramolecular coupling, or hybridization, at the molecular level can lead to intramolecular coupling at the crystalline level after crystallization of the initial hybrid. One skilled in the art will recognize that the precise binding between the two nucleic acid sequences will serve as a template for subsequent additional crystal growth on the nucleic acid hybrid.

Another example of a nucleating agent with close lattice match characteristics is the specific binding between a specific antibody and its antigen, or vice versa. This intramolecular coupling at the molecular level can lead to intramolecular coupling at the crystalline level after crystallization of the initial hybrid.

One skilled in the art will readily appreciate the number of biological compounds that may be used in the disclosed method. Lattice characteristics of these compounds can be obtained from reference materials or by direct measurement. Similarly, the lattice dimensions of proteins are readily obtainable to one in the art. One such example of a source for this information can be found in *Lattice Structure of Proteins*, NIST/NASA/CARB Biological Macromolecule Crystallization Database, Ver. 3.0, (March 1994), which is herein incorporated by reference, for all its teachings and for all the specific teachings of typical proteins.

Once the polypeptide is crystallized, there results a mixture of crystal(s) attached to the nucleating agent(s) and unattached crystals. It is beneficial to separate the attached crystals into an isolated format away from the unattached crystals so that a composition of attached crystals substantially free of unattached crystals is provided. Any number of methods may be used to separate a crystal, a plurality of crystals, or a majority of crystals attached to the nucleating agent from the unattached crystals. This achieves the isolation of the pure crystals, which are attached to the nucleating agent, from the impure crystals, which are unattached. For example, the attached crystal may be isolated by hand selection or by sieving. Alternatively, the attached crystal may be isolated from an unattached crystal based on a magnetic property of the nucleating agent or isolating the nucleating agent with an attached crystal from the crystallization mixture based upon its mass, for example through density separation by differential centrifugation. An additional separation technique may include attaching the nucleating agent to a solid support and removing the solid support and its associated nucleating agent from the crystallization mixture after the polypeptide has crystallized on the nucleating agent. Other methods of separating a crystal attached to a nucleating agent from a crystal unattached to a nucleating agent will be apparent to a skilled practitioner in the art.

Additionally, crystals that are attached to a nucleating agent may be separated from that nucleating agent through any number of means. For example, the highly purified polypeptide crystal may be physically separated, either in part or in whole, from the nucleating agent by detaching the crystal from the nucleating agent, by for example, shearing, or by dissolving the purified polypeptide crystal in a suitable solvent and then removing this solubilized polypeptide from the nucleating agent, thereby separating the two.

In one embodiment, the separation of this invention achieves separating the polypeptide crystal attached to the nucleating agent from the other components in the crystallization mixture, so that one may have possession of a highly purified crystal attached to the nucleating agent apart from contaminants, from any other components of the crystallization mixture, and from any crystals that crystallized unattached to a nucleating agent. In a further embodiment, by removing the nucleating agent from crystals to which it is attached, the polypeptide crystal is separated and isolated from the nucleating agent as well as from the other components in the crystallization mixture, so that one may have possession of a highly purified polypeptide apart from contaminants, from any other components of the crystallization mixture, from any crystals that crystallized unattached to a nucleating agent, and from the nucleating agent to which the highly purified polypeptide crystallized. Moreover, one may convert the polypeptide crystal to a non-crystalline form, thereby achieving a separation or isolation of highly pure polypeptide. Thus, one may have possession of a highly purified polypeptide crystal or a highly purified polypeptide that may be used in later analyses or for other uses.

In this invention, the crystals attached to the nucleating agent are of significantly higher purity, that is, they have a lower amount of contaminants, than crystals that are unattached to a nucleating agent or those which nucleate spontaneously. In preferred embodiments, the term "high purity" relates to a level of purity not before repeatable through conventional polypeptide crystallization. In the crystallization art, a common technique for determining the "quality" of a crystal is often limited to visual inspection of crystals to determine whether they are morphologically correct, such as whether they have distinct and symmetrical faces and edges, whether the crystal has structural cracks, and whether the crystal is clear rather than cloudy or mottled. Thus, the use of the term high quality in the art is not the same as the use of the term "high purity" as used herein. A major technique used in the past to determine the purity of a polypeptide crystal is the X-ray diffraction pattern these crystals yield when subjected to x-ray diffraction analysis. This technique, however, does not yield a quantitative value of crystal purity but rather a qualitative assessment since the X-ray pattern observed only allows the detection of high impurity levels that make a diffraction difference at the unit cell dimensions.

Once the polypeptide is crystallized on a nucleating agent and separated from crystals unattached to the nucleating agent, any number of methods of biochemical analysis typically used in the art can give specific information about the actual content of the crystals. For example, the polypeptide crystals can be resolubilized and then subjected to quantitative analytical techniques such as spectrophotometry, electrophoresis, isoelectric focusing, sequencing, ultrafiltration, dialysis, chromatography based on mass, charge, or affinity, assay kinetics, or combinations of these techniques, and the like.

Accordingly, the present invention can achieve a polypeptide crystal that is at least 99.65% pure, more preferably at least 99.70% pure, more preferably at least 99.75% pure, more preferably at least 99.80% pure, more preferably at least 99.85% pure, more preferably at least 99.90% pure, more preferably at least 99.92% pure, more preferably at least 99.94% pure, more preferably at least 99.96% pure, more preferably at least 99.97% pure, more preferably at least 99.98% pure, and more preferably at least 99.99% pure. Purity, as used herein, relates to any contaminant that the polypeptide is being purified and isolated away from and depends on the specifics of the crystallization itself The particular contaminants will be apparent to a skilled practitioner in the art. Of course, the presence of the attached nucleating agent is not considered in the purity calculation. The purity of a crystallized polypeptide relates to the contamination of the desired polypeptide in the crystal by a different or unrelated polypeptide in the same crystal, or by an undesirable compound or molecule unrelated to the polypeptide. For example, a crystal that has both lysozyme and ovotransferrin in the same crystal constitutes a crystal of lysozyme that is contaminated with ovotransferrin, or a ovotransferrin crystal that is contaminated with lysozyme, depending on the desired crystallized polypeptide. Alternatively, a contaminant of a polypeptide crystal may be a nucleic acid that was present in the mixture containing the polypeptide being crystallized. A contaminant in the mixture can comprise more than a single type species of a contaminant. For example, a crystallization mixture may contain two or more types of contaminants. For another example, a mixture may contain several different species of polypeptides and other contaminants in the same mixture, where a specific species of polypeptide or more than one specific species of polypeptide is being crystallized on their respective nucleating agent. Alternatively, a mixture may contain more than one polypeptide species, nucleic acids, detergents, etc., in addition to the polypeptide species being crystallized. Other contaminants include, but are not limited to amino acids, nucleotides, ions, salts, carbohydrates, precipitants, cellular components such as micro and macromolecular structures, and the like.

As used herein, the term "yield" relates to the mass of the purer form of the polypeptide recovered from the crystallization mixture. In a crystallization mixture which includes an exogenous nucleating agent of this invention, yield is the total mass of polypeptide crystal obtained from the crystallization procedure that is attached to the nucleating agent over the total mass of polypeptide in the crystallization mixture. If the crystallization reaction occurs without an exogenous nucleating agent, the yield is the total mass of crystallized polypeptide over the total mass of polypeptide in the crystallization mixture. The term "high yield" then relates to a comparison of these two yields. For example, the control yield minus the yield for crystals attached to an exogenous nucleating agent multiplied by 100 and then divided by the control yield gives a yield of the crystals attached to the nucleating agent as a percent deviation from the control yield. The term "high yield" applies to (1) a polypeptide crystallization in the presence of an exogenous nucleating agent where this percent deviation relative to the control is less than 22% if the yield is lower with an exogenous nucleating agent than the control, or (2) any yield with an exogenous nucleating agent which is higher than the control yield.

Utility

The present invention has many useful and practical utilities as noted herein. For example, the present invention provides for a method of crystallizing polypeptides in high purity. These highly purified polypeptide crystals may be used in X-ray diffraction studies for polypeptide structural analysis in rational drug design. Alternatively, the present invention provides a method for highly purifying polypeptide crystals whose polypeptide may later be used as a drug.

The following example is put forth so as to provide those of ordinary skill in the art with a complete disclosure and description of how the purified polypeptides claimed herein are made and evaluated, and is intended to be purely exemplary of the invention and is not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric.

EXAMPLE

Analysis of Chicken Egg White Lysozyme Crystallized on Various Exogenous Mineral Substrates Reagents and Substrates. Experiments were conducted using chicken-white lysozyme (Sigma, Grade I, Lot 111H7010, MW~14,600). The lysozyme was crystallized three times, dialyzed, and lyophilized by the supplier. The Sigma product is 95% protein with a balance of buffer salts as sodium acetate and sodium chloride and 0.5 to 2.5% albumin.

Amounts of lysozyme were weighed with an accuracy of 0.1 mg using an electronic balance (Ohaus, AP250D). The lysozyme was then dissolved in a sodium acetate buffer. (0.1M, pH 4.0) The stock lysozyme solution was prepared at a concentration of 50 mg/ml. The solution was then divided into 2 ml aliquots and stored at 17° C. until needed. The nucleating agents chosen for this study were magnetite, lepidolite, topaz, NC-apophyllite (a non-cleavable surface of apophyllite that does not have a lattice match to lysozyme), and apophyllite. (Purchased from Ward's Natural Science Company, Rochester, N.Y.). The areal lattice match between lysozyme and apophyllite was calculated as follows:

The two linear lattice dimensions for lysozyme are 79.1 Å and 37.9 Å, the two linear lattice dimensions for apophyllite are 38.1 Å (12.7Å×3) and 79 Å (15.8Å×5).

$$\frac{(79\text{Å} \times 38.1\text{Å}) - (79.1\text{Å} \times 37.9\text{Å})}{(79.1\text{Å} \times 37.9\text{A})} = 0.40\% \text{ areal mismatch}$$

The areal mismatch of the other exogenous nucleating agents were calculated in a similar manner. Relative to the areal crystalline lattice of lysozyme, the percent areal mismatch of the areal lattice of apophyllite, topaz, and lepidolite, are 0.40%, 9.6%, and 20.8%, respectfully. Thus, their lattice match is 99.60%, 90.40%, and 79.20%, respectfully. Magnetite and NC-apophyllite do not have defined unit cells and lattice dimensions; therefore, these areal lattice mismatches cannot be calculated, and so, these minerals do not have a lattice match. Thus, these minerals represent nucleating agents whose areal mismatch clearly exceed 15% to that of lysozyme. These substrates were cleaved for the desired surface area (surface diameter approximately 850 μm) and then sieved. A typical crystallization well contained one mineral particle.

Lysozyme was crystallized by the vapor diffusion method on plates (Product number 7220, Corning, Corning, N.Y.) (General discussion of the vapor diffusion technique are set forth in *Crystallization of Nucleic Acids and Proteins: A Practical Approach*, ed. A. Ducruix and R. Giegé, Oxford University Press, New York, 1992). Each depression plate consisted of nine crystallization wells. The depression plates were siliconized with Sigmacote (Sigma # SL-2) prior to beginning crystallization trials. The pre-crystallization solution consisted of lysozyme, ovotransferrin (Sigma Chemical Co., Prod. No. C-0755, Lot No. 107F8020) (5% of total protein), sodium acetate buffer (0.1M) at pH 4.0, and 2.5 wt % NaCl as precipitating agent in high purity water (HPLC grade, J. T. Baker Prod. No. 4218-03). All pre-crystallization solutions were passed through a 0.2 μm pore filter (Nalgene) and used immediately. Each well of the crystallization plate was supplied with 150 μl of the pre-crystallization solution.

Protein Crystallization. After the solutions were filtered and pipetted into the nine wells of the depression plate, the mineral substrates were deposited into the pre-crystallization solutions. The depression plates were placed and sealed in plastic chambers (Model 156C, Tri State Plastics, Dixon, Ky.) that contained 30 ml of precipitating solution consisting of 5.0 wt % NaCl in high purity water (HPLC grade, J. T. Baker Prod. No. 4218-03). The chambers were maintained at 18° C. by being immersed in water circulating from a constant temperature bath. Protein crystals were recovered from the crystallization solution after cessation of crystal growth was observed. Cessation of protein crystal growth was generally achieved after seven days.

Crystal Attachment. The degree of attachment between protein crystals and mineral substrate were visually estimated by microscopy (Nissho Seimitsu Kogaku SS microscope, 4× magnification). The percent of crystals attached to the mineral substrate was quantified by taking a ratio between the number of crystals attached to the substrate to the total number of crystals present in the well. The ratio was then multiplied by 100.

Crystal Analysis. After visual observations were performed, all remaining protein solution in each well was aspirated with a pipette and stored, leaving the crystals behind. Next, crystals attached to a mineral substrate as well as those not attached to a mineral substrate were washed with 5 wt % NaCl, solubilized with 100 μl of HPLC-Grade water (J. T. Baker Prod. No. 4218-03) and frozen at −17° C.

Samples selected for purity analysis were removed from the freezer and thawed in a water bath containing tap water at room temperature. The samples were analyzed by high performance liquid chromatography (HPLC) (Shimadzu). Samples were passed through a reverse-phase column C18 300 Å column (0.9×25 cm) (Rainin).

Mixtures of lysozyme and ovotransferrin were injected into the HPLC to evaluate the separation of peaks achieved and determine retention times. It was found that under the recommended conditions for the C18 300 Å column, ovotransferrin had a retention time equivalent to that of lysozyme. The elution protocol used for separating lysozyme and ovotransferrin therefore required refinement to eliminate ambiguity between peaks of lysozyme and ovotransferrin. The refined protocol uses the following conditions:

| SOLVENT SYSTEM | |
| --- | --- |
| Buffer A: | 0.1% TFA in water |
| Buffer B: | 0.1% TFA in acetonitrile |
| Flow Rate: | 0.75 ml/min. |
| Temperature of Column: | Room Temp (23° C.) |
| Sample injection: | 60 μl |

Samples were chromatographed in 60 min. using a linear gradient of 17 min. from 15 to 40% buffer B continuing to 40 min. from 40 to 55% buffer B. Absorbance of the eluate was recorded at a wavelength of 230 nm at a detector sensitivity of 1 AUFS. (Shimadzu detector). The reproducibility of the revised protocol was tested by analyzing a lysozyme stock solution (50.1 mg/ml) nine successive times. The standard deviation of the lysozyme peak area was 0.11% of the mean. Student T-tests at a 95% confidence interval were used to examine the data.

High concentrations of the solubilized recovered crystals were injected into the HPLC to determine whether, and to what extent, ovotransferrin might be present in the lysozyme crystals. From chromatograms it was possible to determine the area of the ovotransferrin peak. The mass of ovotransferrin in the sample was calculated by using a HPLC calibration curve.

Crystal Protein Content. A dye binding spectrophotometric assay kit (Bio-Rad Protein Assay # 500-0001, Bio-Rad Laboratories, Hercules, Calif.) was used to determine the total mass of protein present in samples injected into the HPLC. The purity of the polypeptide lysozyme was calculated for this particular experiment as the total protein obtained in a sample minus the mass of ovotransferrin in that sample, divided by the mass of the total protein in the sample, multiplied by 100.

Statistical analysis of the data was performed by using a statistical package (Mini-Tab, Ver. 10.1, Minitab, Inc., State College, Pa.). An analysis of variance using a 95% confidence interval was used to examine the data. Additionally, two-sample T-tests at a 95% confidence interval were used when comparing two observations.

Results

Figure 1:
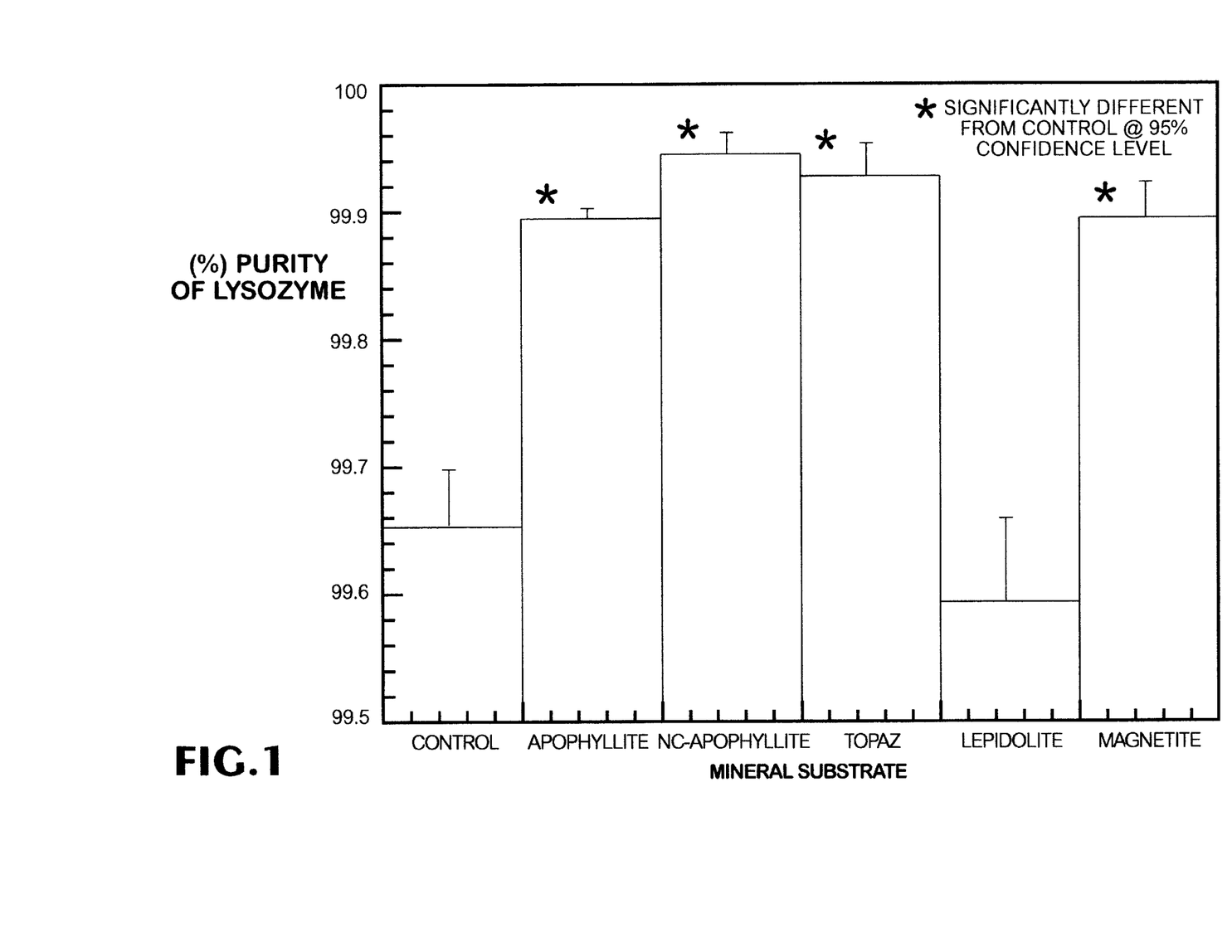
FIG. 1 shows the purity of lysozyme crystals grown in the absence of exogenous mineral nucleating agents (control) compared to lysozyme crystals attached to exogenous mineral nucleating agents (mineral substrate).

Purity of Crystals Attached to Nucleating Agent Compared to Purity of Spontaneously Nucleating Crystals. Crystals obtained from a mixture of lysozyme and ovotransferrin (5% of total protein) were removed from the crystallization mixture and analyzed for their specific protein content by HPLC as described above. The control crystals were obtained from crystallization wells that did not contain a nucleating agent and therefore were the products of spontaneous nucleation. FIG. 1 illustrates that lysozyme crystals grown in the presence of and attached to certain nucleating agents were significantly higher in purity than control crystals. Lysozyme crystals that spontaneous nucleated averaged 99.65% in purity whereas lysozyme crystals attached to apophyllite, NC-apophyllite, topaz, and magnetite averaged at least 99.90% in purity. Lysozyme crystals grown on lepidolite, which has an approximate 20% crystal lattice mismatch to the crystal lattice of lysozyme, were statistically equivalent in purity to the control crystals.

Figure 2:
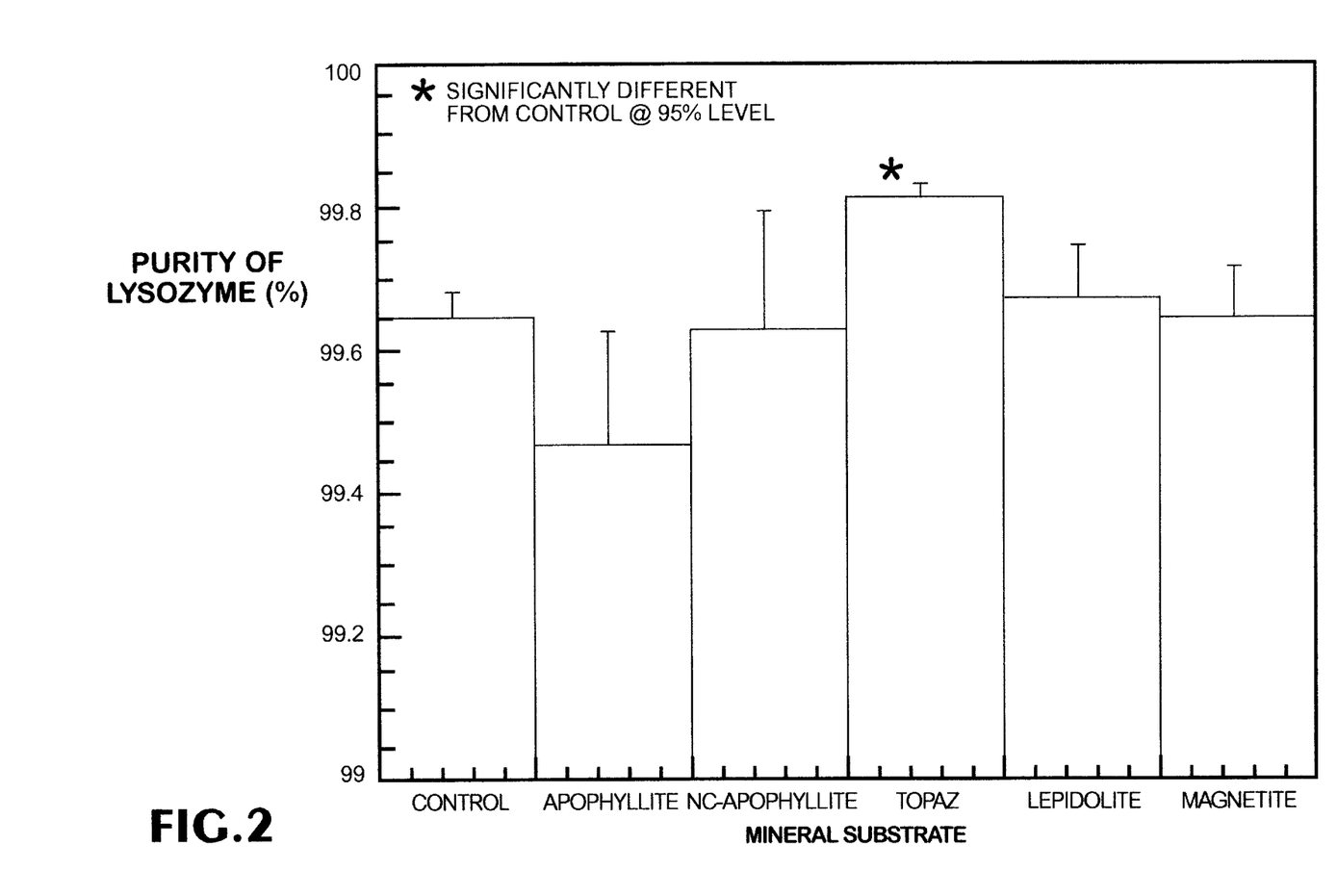
FIG. 2 shows the purity of lysozyme crystals grown in the absence of exogenous mineral nucleating agents (control) compared to lysozyme crystals grown in the presence of exogenous mineral nucleating agents but not attached to exogenous mineral nucleating agents (mineral substrate).
Figure 3:
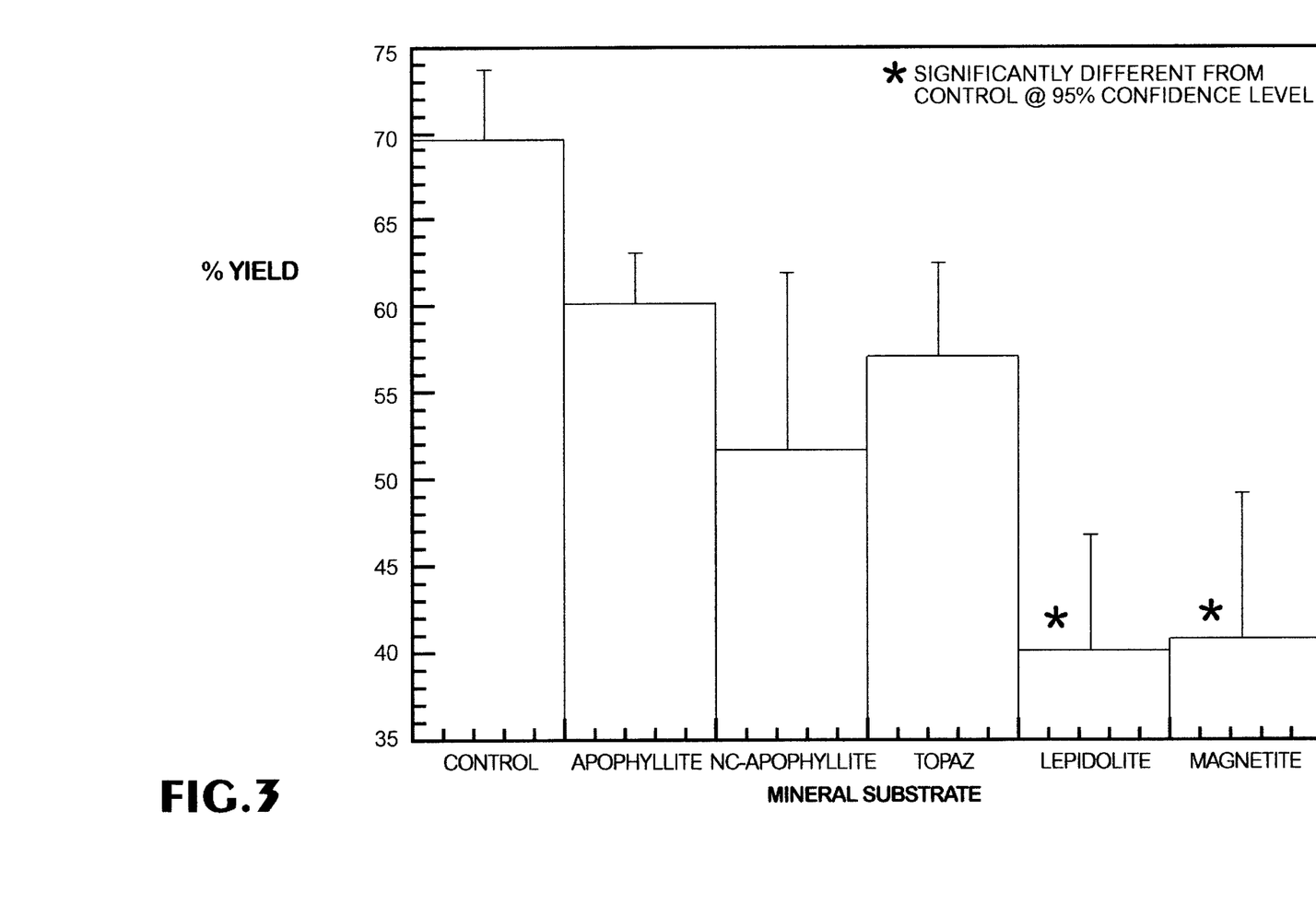
FIG. 3 shows the yield of recovered protein from crystals attached to exogenous mineral nucleating agents compared to crystals grown in the absence of exogenous mineral nucleating agents (mineral substrate).

In FIGS. 1–3, the error bars represent the standard error obtained by analyzing crystals in three crystallization wells for NC-apophyllite and topaz, in four wells for lepidolite, in eight wells for magnetite, in fourteen wells for apophyllite, and in eighteen wells for the control. In each case, all attached crystals in a well were pooled and analyzed for purity and yield. Also, in each case, all non-attached crystals in a well were pooled and analyzed for purity and yield.

Crystals that were grown in the presence of the exogenous nucleating agents but were not attached to those nucleating agents did not have as high a purity as those attached to the nucleating agent, except for lepidolite. (FIGS. 1 and 2). The highest purity of these unattached crystals was always less than 99.85%. Lysozyme crystals grown in the presence of but unattached to the nucleating agent topaz, were significantly higher in purity than the control crystals, but these crystals were still significantly lower in purity than lysozyme crystals attached to the same nucleating agent. Additionally, the lysozyme crystals grown in the presence of and attached to an exogenous mineral nucleating agent with a close lattice match to the lattice of lysozyme were always of a higher purity than those crystals unattached to the same mineral nucleating agent and of the control.

These unattached crystals result from spontaneous nucleation and were generally equivalent in purity to the control crystals. Experiments have shown that the unattached crystals were not the result of small nucleating agents that originated from the exogenous nucleating agent through mechanical disturbance, small material sloughed off from the exogenous nucleating agent, or from any nucleating agent accidentally added to the crystallization well.

Crystal Yields. The amount of protein recovered from the crystallization mixture was highly correlated to the dimension differences between the crystal lattice of the nucleating agent and the crystal lattice of lysozyme. (FIG. 3). Lepidolite and magnetite, those mineral nucleating agents with the least lattice match to lysozyme, exhibited much lower yields of attached lysozyme crystals than the other nucleating agents with a closer lattice match.

The crystallization yield in the presence of an exogenous nucleating agent is the total mass of polypeptide crystal obtained from the crystallization procedure that is attached to the nucleating agent over the total mass of polypeptide in the crystallization mixture. The crystallization yield without an exogenous nucleating agent is the total mass of crystallized polypeptide over the total mass of polypeptide in the crystallization mixture. The term "high yield" then relates to a comparison of these two yields. For example, the control yield minus the yield for crystals attached to an exogenous nucleating agent multiplied by 100 and then divided by the control yield gives a yield of the crystals attached to the nucleating agent as a percent deviation from the control yield. Here, the term "high yield" applies to a polypeptide crystallization in the presence of an exogenous nucleating agent where this percent deviation relative to the control is less than 22%. The calculated percent yield deviations relative to the control in this experiment were 13, 26, 18, 51, and 41, for the exogenous nucleating agents apophyllite, NC-apophyllite, topaz, lepidolite, and magnetite, respectfully. The only nucleating agents that exhibited a high yield of the high purity polypeptide crystals (those crystals attached to the nucleating agent) were apophyllite and topaz, both of which are within the areal lattice match parameter of at least 85%. Those nucleating agents with an areal lattice match below 85% did not exhibit a high yield of high purity polypeptide crystals.

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and example be considered as exemplary only, with a true scope and spirit of the invention being indicated by the following claims.

What is claimed is:

1. A method of highly purifying a polypeptide from a contaminant by crystallization comprising:
   (a) contacting a mixture containing uncrystallized polypeptides and a contaminant with an exogenous nucleating agent that has an areal lattice match of at least 90.4% to the polypeptide,
   (b) crystallizing the polypeptides, thereby forming at least one crystal of the polypeptide attached to the nucleating agent, the attached crystal being of a high purity, and at least one polypeptide crystal unattached to the nucleating agent, the unattached crystal being of a lower purity than the attached crystal, and
   (c) separating the crystal attached to the nucleating agent from the crystal unattached to the nucleating agent.

2. A method of purifying a polypeptide in a high purity and in a high yield from a contaminant by crystallization comprising:
   (a) contacting a mixture containing uncrystallized polypeptides and a contaminant with an exogenous nucleating agent that has an areal lattice match of at least 90.4% to the polypeptide,
   (b) crystallizing the polypeptides, thereby forming at least one crystal of the polypeptide attached to the nucleating agent, the attached crystal being of a high purity and produced in a high yield, and at least one crystal unattached to the nucleating agent, the unattached crystal being of a lower purity than the attached crystal, and
   (c) separating the crystal attached to the nucleating agent from the crystal unattached to the nucleating agent.

3. The method of claim 1, wherein the separation in step (c) comprises separating a plurality of crystals attached to the nucleating agent from the crystal unattached to the nucleating agent.

4. The method of claim 2, wherein the separation in step (c) comprises separating a plurality of crystals attached to the nucleating agent from the crystal unattached to the nucleating agent.

5. The method of claim 1, wherein the separation in step (c) comprises separating a majority of the crystals attached to the nucleating agent from the crystal unattached to the nucleating agent.

6. The method of claim 2, wherein the separation in step (c) comprises separating a majority of the crystals attached to the nucleating agent from the crystal unattached to the nucleating agent.

7. The method of claim 1, wherein the crystallization step (b) comprises increasing the concentration of the polypeptide in the mixture.

8. The method of claim 1, wherein the crystallization step (b) comprises decreasing the temperature of the mixture containing the polypeptide and the contaminants.

9. The method of claim 2, wherein the crystallization step (b) comprises increasing the concentration of the polypeptide in the mixture.

10. The method of claim 2, wherein the crystallization step (b) comprises decreasing the temperature of the mixture containing the polypeptide and the contaminants.

11. The method of claim 1, wherein the separation step (c) comprises a separation by hand, by magnetic separation, by density separation, or by removing a solid support from the mixture to which the nucleating agent with its attached crystal is attached.

12. The method of claim 2, wherein the separation step (c) comprises a separation by hand, by magnetic separation, by density separation, or by removing a solid support from the mixture to which the nucleating agent with its attached crystal is attached.

13. The method of claim 1, wherein the nucleating agent is a mineral.

14. The method of claim 2, wherein the nucleating agent is a mineral.

15. The method of claim 1, further comprising separating the polypeptide crystal attached to the nucleating agent from the nucleating agent.

16. The method of claim 2, further comprising separating the polypeptide crystal attached to the nucleating agent from the nucleating agent.

17. The method of claim 15, wherein the crystal attached to the nucleating agent is separated from the nucleating agent by shearing the crystal from the nucleating agent.

18. The method of claim 15, wherein the crystal attached to the nucleating agent is separated from the nucleating agent by detaching the crystal from the nucleating agent by solubilizing the crystal and then separating the detached nucleating agent from the polypeptide.

19. The method of claim 16, wherein the crystal attached to the nucleating agent is separated from the nucleating agent by shearing the crystal from the nucleating agent.

20. The method of claim 16, wherein the crystal attached to the nucleating agent is separated from the nucleating agent by detaching the crystal from the nucleating agent by solubilizing the crystal and then separating the detached nucleating agent from the polypeptide.

21. A composition consisting of at least one polypeptide crystal attached to an exogenous nucleating agent, wherein the polypeptide was crystallized by contacting the polypeptide with the exogenous nucleating agent, wherein the exogenous nucleating agent has an areal lattice match of at least 90.4% to the polypeptide, and wherein the polypeptide is not lysozyme, canavalin, concanavalin B, or beef liver catalase.

22. A composition consisting essentially of at least one polypeptide crystal attached to an exogenous nucleating agent, wherein the polypeptide was crystallized by contacting the polypeptide with the exogenous nucleating agent, wherein the exogenous nucleating agent has an areal lattice match of at least 90.4% to the polypeptide, and wherein the polypeptide is not lysozyme, canavalin, concanavalin B, or beef liver catalase.

23. A composition comprising at least one polypeptide crystal attached to an exogenous nucleating agent, wherein the polypeptide was crystallized by contacting the polypeptide with the exogenous nucleating agent, wherein the exogenous nucleating agent has an areal lattice match of at least 90.4% to the polypeptide, and wherein the polypeptide is not lysozyme, canavalin, concanavalin B, or beef liver catalase.

24. The composition of claim 21, wherein the purity of the crystal is at least 99.85%.

25. The composition of claim 22, wherein the purity of the crystal is at least 99.85%.

26. The composition of claim 23, wherein the purity of the crystal is at least 99.85%.

27. A composition consisting of a polypeptide crystal which was crystallized by contacting the polypeptide to an exogenous nucleating agent that has an areal lattice match of at least 90.4% to the polmpeptide and that has been separated from the nucleating agent, wherein the purity of the crystal is at least 99.85%, and wherein the polypeptide is not lysozyme, canavalin, concanavalin B, or beef liver catalase.

28. A composition consisting essentially of a polypeptide crystal which was crystallized by contacting the polypeptide to an exogenous nucleating agent that has an areal lattice match of at least 90.4% to the polypeptide and that has been separated from the nucleating agent, wherein the purity of the crystal is at least 99.85%, and wherein the polypeptide is not lysozyme, canavalin, concanavalin B, or beef liver catalase.

29. A composition comprising a polypeptide crystal which was crystallized by contacting the polypeptide to an exogenous nucleating agent that has an areal lattice match of at least 90.4% to the polypeptide and that has been separated from the nucleating agent, wherein the purity of the crystal is at least 99.85%, and wherein the polypeptide is not lysozyme, canavalin, concanavalin B, or beef liver catalase.

30. A composition consisting of a polypeptide which was crystallized by contacting the polypeptide to an exogenous nucleating agent that has an areal lattice match of at least 90.4% to the polypeptide and that has been separated from the nucleating agent, wherein the purity of the crystal is at least 99.85%, and wherein the polypeptide is not lysozyme, canavalin, concanavalin B, or beef liver catalase.

31. A composition consisting essentially of a polypeptide which was crystallized by contacting the polypeptide to an exogenous nucleating agent that has an areal lattice match of at least 90.4% to the polypeptide and that has been separated from the nucleating agent, wherein the purity of the crystal is at least 99.85%, and wherein the polypeptide is not lysozyme, canavalin, concanavalin B, or beef liver catalase.

32. A composition comprising a polypeptide which was crystallized by contacting the polypeptide to an exogenous nucleating agent that has an areal lattice match of at least 90.4% to the polypeptide and that has been separated from the nucleating agent, wherein the purity of the crystal is at least 99.85%, and wherein the polypeptide is not lysozyme, canavalin, concanavalin B, or beef liver catalase.

33. A highly purified polypeptide crystal obtained by the method of claim 1.

34. A highly purified polypeptide crystal obtained by the method of claim 2.

35. A highly purified polypeptide crystal obtained by the method of claim 19.

36. A highly purified polypeptide crystal obtained by the method of claim 20.

37. The method of claim 1, wherein the polypeptide is not lysozyme, canavalin, concanavalin B, or beef liver catalase.

38. The method of claim 2, wherein the polypeptide is not lysozyme, canavalin, concanavalin B, or beef liver catalase.

39. A method of highly purifying a biological compound from a contaminant by crystallization comprising:
  (a) contacting a mixture containing uncrystallized biological compounds and a contaminant with an exogenous nucleating agent that has an areal lattice match of at least 90.4% to the biological compound,
  (b) crystallizing the biological compounds, thereby forming at least one crystal of the biological compound attached to the nucleating agent, the attached crystal being of a high purity, and at least one biological compound crystal unattached to the nucleating agent, the unattached crystal being of a lower purity than the attached crystal, and
  (c) separating the crystal attached to the nucleating agent from the crystal unattached to the nucleating agent.

40. A method of purifying a biological compound in a high purity and in a high yield from a contaminant by crystallization comprising:

(a) contacting a mixture containing uncrystallized biological compounds and a contaminant with an exogenous nucleating agent that has an areal lattice match of at least 90.4% to the biological compound, (b) crystallizing the biological compounds, thereby forming at least one crystal of the biological compound attached to the nucleating agent, the attached crystal being of a high purity and produced in a high yield, and at least one crystal unattached to the nucleating agent, the unattached crystal being of a lower purity than the attached crystal, and (c) separating the crystal attached to the nucleating agent from the crystal unattached to the nucleating agent.

41. A composition comprising at least one biological compound crystal attached to an exogenous nucleating agent, wherein the biological compound was crystallized by contacting the biological compound with the exogenous nucleating agent, wherein the exogenous nucleating agent has an areal lattice match of at least 90.4% to the biological compound, and wherein the biological compound is not lysozyme, canavalin, concanavalin B, or beef liver catalase.

42. A composition comprising a biological compound crystal which was crystallized by contacting the biological compound to an exogenous nucleating agent that has an areal lattice match of at least 90.4% to the biological compound and that has been separated from the nucleating agent, wherein the purity of the crystal is at least 99.85%, and wherein the biological compound is not lysozyme, canavalin, concanavalin B, or beef liver catalase.

43. A composition comprising a biological compound which was crystallized by contacting the biological compound to an exogenous nucleating agent that has an areal lattice match of at least 90.4% to the biological compound and that has been separated from the nucleating agent, wherein the purity of the biological compound is at least 99.85%, and wherein the biological compound is not lysozyme, canavalin, concanavalin B, or beef liver catalase.

44. The method of claim 1, wherein the exogenous nucleating agent has a lattice match of at least 99.60%.

* * * * *